(12) United States Patent
Mo et al.

(10) Patent No.: US 8,951,200 B2
(45) Date of Patent: Feb. 10, 2015

(54) APPARATUSES AND METHODS FOR COMPUTER AIDED MEASUREMENT AND DIAGNOSIS DURING ULTRASOUND IMAGING

(75) Inventors: Ruoli Mo, Wuxi (CN); Danhua Zhao, Wuxi (CN); Mingchang Zhao, Wuxi (CN)

(73) Assignee: Chison Medical Imaging Co., Ltd., Wuxi (CN)

( * ) Notice: Subject to any disclaimer, the term of this patent is extended or adjusted under 35 U.S.C. 154(b) by 0 days.

(21) Appl. No.: 13/572,562

(22) Filed: Aug. 10, 2012

(65) Prior Publication Data
US 2014/0046185 A1 Feb. 13, 2014

(51) Int. Cl.
*A61B 8/14* (2006.01)
(52) U.S. Cl.
USPC .......................................................... 600/443
(58) Field of Classification Search
USPC .......................................................... 600/443
See application file for complete search history.

(56) References Cited

U.S. PATENT DOCUMENTS

| 6,063,030 | A * | 5/2000 | Vara et al. .................... 600/437 |
| 6,638,223 | B2 | 10/2003 | Lifshitz |
| 6,855,114 | B2 * | 2/2005 | Drukker et al. ............... 600/443 |
| 7,022,075 | B2 | 4/2006 | Grunwald |
| 8,016,759 | B2 | 9/2011 | Lee |
| 2005/0010445 | A1 | 1/2005 | Krishnan |
| 2008/0002873 | A1 * | 1/2008 | Reeves et al. ................. 382/133 |
| 2008/0119731 | A1 * | 5/2008 | Becerra et al. ............... 600/437 |
| 2009/0131793 | A1 | 5/2009 | Stonefield |
| 2009/0268952 | A1 * | 10/2009 | Schaffer et al. ............... 382/128 |
| 2010/0004539 | A1 * | 1/2010 | Chen et al. .................... 600/445 |
| 2010/0022881 | A1 * | 1/2010 | Fujita et al. .................... 600/445 |
| 2010/0094132 | A1 | 4/2010 | Hansen |
| 2010/0145195 | A1 | 6/2010 | Hyun |
| 2010/0266173 | A1 | 10/2010 | Lorenz |
| 2011/0288414 | A1 * | 11/2011 | Yu et al. ........................ 600/443 |
| 2013/0072795 | A1 * | 3/2013 | Mo et al. ....................... 600/443 |
| 2013/0289405 | A1 * | 10/2013 | WANG et al. ................ 600/440 |

FOREIGN PATENT DOCUMENTS

| CN | 101040245 A | 9/2007 | |
| EP | 2056190 A1 * | 5/2009 | ............... G06F 9/44 |
| WO | WO 2006126131 A1 * | 11/2006 | |
| WO | WO 2009140690 A2 * | 11/2009 | ........... A61B 5/0402 |

* cited by examiner

*Primary Examiner* — Long V Le
*Assistant Examiner* — Kevin Pontius
(74) *Attorney, Agent, or Firm* — Finnegan, Henderson, Farabow, Garrett & Dunner LLP (57) ABSTRACT

An ultrasound imaging apparatus configured with a touch screen display and computer aided measurement and/or diagnosis capability. In response to a touch input, image parameters for the computer aided measurement and/or diagnosis are determined from an analysis of the ultrasound image. A touch screen user interface allows the user to further adjust the parameters and/or other system parameters for the computer aided measurement and/or diagnosis in an interactive way. The computer aided measurement can be used directly for the computer aided diagnosis for improved accuracy and user experience.

19 Claims, 4 Drawing Sheets

APPARATUSES AND METHODS FOR COMPUTER AIDED MEASUREMENT AND DIAGNOSIS DURING ULTRASOUND IMAGING

FIELD OF TECHNOLOGY

The disclosure of the present application relates to, but not limited to, ultrasound imaging and user input processing for ultrasound imaging.

BACKGROUND

The conventional computer aided measurement (CAM) and computer aided diagnosis (CAD) technologies used in medical ultrasound imaging systems have a number of problems and limitations.

In a typical system, measurements are performed based on input generated using a touchpad or trackball and a number of buttons on the keyboard. Such a measurement system is slow, unintuitive, cumbersome, and inaccurate.

Conventional CAD technologies use predefined image processing algorithms and existing knowledge database to help doctors make diagnosis based on medical imaging, such as ultrasound imaging.

At least some embodiments of the present invention overcome some of the limitations of the current measurement technologies and diagnosis technologies by at least utilizing a touch screen based user interface.

BRIEF DESCRIPTION OF THE DRAWINGS

The embodiments disclosed in the presented application are illustrated by way of example and not limitation in the figures of the accompanying drawings in which like references indicate similar elements.

SUMMARY OF THE DESCRIPTION

In one embodiment, an ultrasound imaging apparatus is configured with a touch screen display and computer aided measurement and/or diagnosis capability. In response to a touch input, geometric parameters for the computer aided measurement and/or diagnosis are determined from an analysis of the ultrasound image. A touch screen user interface allows the user to further adjust the geometric parameters and/or other parameters for the computer aided measurement and/or diagnosis in an interactive way. The computer aided measurement can be used directly for the computer aided diagnosis for improved accuracy and user experience.

In one aspect, an ultrasound imaging apparatus, includes: an ultrasound transducer; a beamformer configured to control the ultrasound transducer; an image processor coupled with the ultrasound transducer to generate an ultrasound image; a touch screen display coupled with the image processor to display the ultrasound image; a touch processor coupled with the touch screen display to receive and process touch input from the entire touch screen display including the portion where the ultrasound image is currently being displayed; a computer aided measurement processor coupled with the touch processor to provide measurement results; and a computer aided diagnosis processor coupled with the touch processor to provide diagnosis results.

In one embodiment, at least one of the touch processor, the image processor, the computer aided measurement processor and the computer aided diagnosis processor includes one of: an application-specific integrated circuit and a field programmable circuit.

In one embodiment, the computer aided diagnosis processor is further coupled to the computer aided measurement processor to receive measurement results for producing the diagnosis results. In one embodiment, the computer aided diagnosis processor operates based on a knowledge base.

In one embodiment, when the touch processor determines that a current touch input received on the touch screen display is for accepting a measurement result from the computer aided measurement processor, the touch processor instructs the computer aided diagnosis processor to perform a diagnosis in an interactive mode.

In one embodiment, when in the interactive mode, the computer aided diagnosis processor is configured to receive at least one input from the touch processor between starting of the diagnosis and presentation of a result for the diagnosis.

In one embodiment, the computer aided measurement processor is coupled with the image processor to present one or more geometric parameters used for producing the measurement results. In one embodiment, the one or more geometric parameters are overlaid on the ultrasound image to allow the user to visually inspect the degree of agreement between the geometric parameters used in the computation and the features in the ultrasound image. In one embodiment, the touch processor is configured to determine whether a currently received touch input is for adjusting the one or more geometric parameters, or for accepting the measurement results.

In one embodiment, the computer aided diagnosis processor is coupled with the image processor to present one or more geometric parameters used for producing the diagnosis results. In one embodiment, the one or more geometric parameters are overlaid on the ultrasound image to allow the user to visually inspect the degree of agreement between the geometric parameters used in the computation and the features in the ultrasound image. In one embodiment, the touch processor is configured to determine whether a currently received touch input is for adjusting the one or more geometric parameters, or for accepting the diagnosis results.

In another aspect, an ultrasound imaging apparatus, includes: an ultrasound transducer; a beamformer configured to control the ultrasound transducer; an image processor coupled with the ultrasound transducer to generate an ultrasound image; a touch screen display coupled with the image processor to display the ultrasound image; a touch processor coupled with the touch screen display to receive and process touch input from the entire touch screen display including the portion where the ultrasound image is currently being displayed, a computer aided processor coupled with the touch processor to determine one or more geometric parameters based on input from the touch processor.

In one embodiment, the computer aided processor includes a computer aided measurement processor to determine at least one of: distance, perimeter, angle, ratio, area, volume, velocity, peak, and heart rate.

In one embodiment, the computer aided processor includes a computer aided diagnosis processor configured to generate diagnosis results based on a knowledge base.

In one embodiment, the computer aided processor is coupled with the image processor and the touch processor to allow interactive adjustment of the one or more geometric parameters via touching the touch screen display.

In one embodiment, the touch processor dynamically adjusts sensitivity and scale of the adjustment of the one or more geometric parameters.

In one embodiment, the one or more geometric parameters are determined based on an initial touch input identifying a location or an area and based on an analysis of the ultrasound image.

In a further aspect, a computer storage medium storing instructions configured to instruct one or more microprocessors of an ultrasound imaging apparatus having an ultrasound transducer, a beamformer and a touch screen display to at least: generate an ultrasound image based on signals from the ultrasound transducer; display the ultrasound image on the touch screen display; receive and process touch input from the entire touch screen display including the portion where the ultrasound image is currently being displayed; determine one or more geometric parameters based on input from the touch processor; provide a user interface allowing interactive adjustment of the one or more geometric parameters via touching the touch screen display; and generate a computer aided measurement or diagnosis result based on the one or more geometric parameters.

The disclosure includes methods and apparatuses which perform these methods, including data processing systems which perform these methods, and computer readable media containing instructions which when executed on data processing systems cause the systems to perform these methods.

Other features will be apparent from the accompanying drawings and from the detailed description which follows.

DETAILED DESCRIPTION

The following description and drawings are illustrative and are not to be construed as limiting. Numerous specific details are described to provide a thorough understanding. However, in certain instances, well known or conventional details are not described in order to avoid obscuring the description.

References to one or an embodiment in the present disclosure are not necessarily references to the same embodiment; and, such references mean at least one. One or more features described in reference to one or an embodiment can be viewed as optional, except in instances where it is apparent from the present description that the presence of other features explicitly requires, or excludes, the presence of such one or more features. Thus, the present disclosure includes all combinations of various features discussed in connection with different references to one or an embodiment, except certain combinations are excluded by ways of explicit discussion or obvious incompatibility.

The present disclosure includes a touch screen based computer aided measurement and/or diagnosis method and system. In at least some embodiments, the measurement process is simplified and made more intuitive and accurate by at least using a touch screen user interface. In at least some embodiments, the CAD is augmented with real time adjustments made using a touch screen user interface to improve the system diagnostic performance. Further details are provided below.

In one embodiment, an ultrasound imaging system is provided with a touch screen based user interface, which is configured to allow users to provide input based at least in part on touching a portion of a touch screen display, on which portion an ultrasound image is currently being displayed while the touching input is received. Allowing a user to provide touch input on the portion of the touch screen display where the ultrasound image is currently being displayed provides a large touch surface for input operations and allow the system to interpret touch input in a context sensitive manner to provide improved user experience.

In one embodiment, the touch screen based user interface allows the user to select, via touching the displayed image, a sub-region to cause the imaging system to perform, change, modify and/or adjust image processing tasks on the displayed image based on the region selected by the user.

In one embodiment, instead of utilizing only the user touch input to select a command that corresponding to the touch input, the touch screen based user interface identifies a command and/or parameters for the execution of the command, based on not only the touch input but also the underlying image that is being touched. In one embodiment, the underlying image is analyzed for the touch screen based user interface; and the analysis result is combined, by the touch screen based user interface, with the touch input to generate intelligently a command appropriate for the processing of the underlying image and corresponding to the touch input.

In one embodiment, the underlying image is a live ultrasound image, which updates periodically according to the most recent signals from the ultrasound transducer. In one embodiment, the underlying image is a frozen ultrasound image, which is based on the signals from the ultrasound transducer during a particular time period and not further updated according to recent signals from the ultrasound transducer.

Systems and methods of a touch screen based user interface in medical ultrasound imaging systems according to some embodiments are described in further details below.

Figure 1:
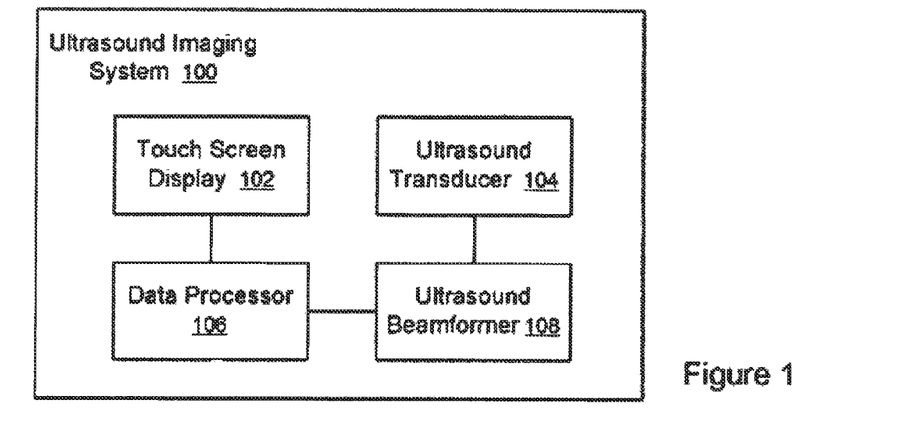
FIG. 1 shows an ultrasound imaging system according to one embodiment.

FIG. 1 shows an ultrasound imaging system according to one embodiment. In FIG. 1, the ultrasound imaging system 100 includes an ultrasound transducer 104, a ultrasound beamformer 108 controlling the ultrasound transducer 104, a touch screen display 102 and a data processor 106 coupled with the ultrasound transducer 104 to generate ultrasound image and coupled with the touch screen display 102 to display the ultrasound image and receive user touch input.

In one embodiment, the data processor 106 is coupled with the ultrasound beamformer 108 to control the ultrasound transducer 104.

Figure 2:
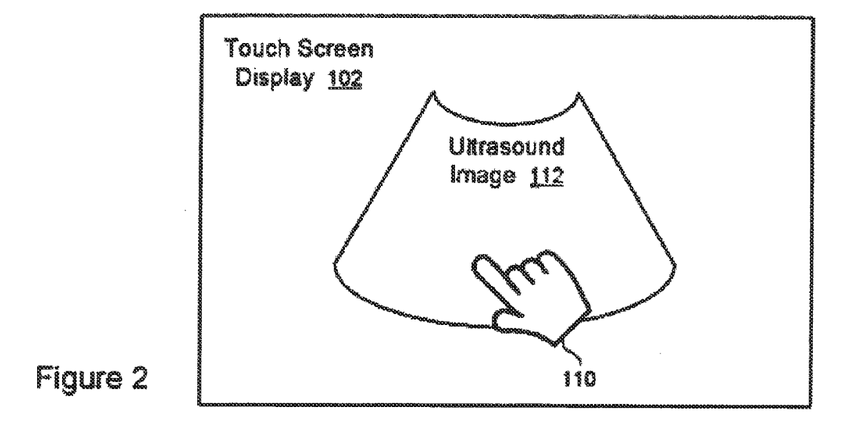
FIG. 2 shows a user interface for an ultrasound imaging system according to one embodiment.

FIG. 2 shows a user interface for an ultrasound imaging system according to one embodiment. In FIG. 2, the ultrasound image 112 generated based on the signals from the ultrasound transducer 104 is displayed in at least portion of the touch screen 102.

In one embodiment, while the ultrasound image 112 is displayed on a portion of the touch screen 102, one or more user interface elements can be displayed concurrently on a different portion of the touch screen 102. Examples of such one or more user interfaces elements include icon image representations of function buttons, which can be selected via touch to activate the execution of pre determined image functions or to invoke other user interfaces to replace the currently displayed user interface elements and/or the ultrasound image 112.

In one embodiment, the ultrasound image 112 is displayed on a portion of the touch screen 102 without concurrently displaying other conventional graphical user interface elements, such as icon buttons, menu buttons, text fields for receiving text input, etc. Some conventional graphical user interface elements may be overlaid on the ultrasound image 112 in response to the user touch input on the ultrasound image 112.

In one embodiment, the user interface is configured to allow the user to touch the ultrasound image 112 displayed on the touch screen 102 to provide the touch input. The touch input is received while the ultrasound image 112 is displayed on the corresponding portion of the touch screen 102 being touched, without the display of a conventional graphical user interface element on the corresponding portion of the touch screen 102.

In one embodiment, the touch input on the ultrasound image 112 is interpreted to generate an image processing command to process the ultrasound image 112 and provide an updated display of the ultrasound image 112.

In one embodiment, different touch inputs are interpreted by the user interface as different touch gestures; and different touch gestures are pre-associated with different, pre-defined user interface functions (e.g., open a predefined user interface, open a pre-identified document or form) and/or image processing functions (e.g., zooming in or zooming out, edge enhancing the image, adjusting the brightness or contrast of the image).

In one embodiment, a touch input represents a user request to improve the image; and the image is analyzed to select an image processing function to improve the image. In one embodiment, the improvement is based on the analysis of a local region touched by the user; and the image processing function may be applied to the same local region, or the entire ultrasound image. In one embodiment, the improvement is applied on a local region touched by the user, based on the image analysis of the location region or the entire ultrasound image.

In one embodiment, the touch gestures are mapped to predefined user interface operations without relying upon the image properties of the ultrasound image 112 being touched. Thus, the same touch gesture applied on different ultrasound images 112 causes the system to apply the same user interface function or image processing function that is pre-associated with the touch gesture.

In one embodiment, a touch gesture includes a sequence of touching operations that identify one or more locations or regions in the ultrasound image 112 and a desired operation based on the identified one or more locations or regions. In one embodiment, the identified one or more locations or regions are used for the desired operation in processing the ultrasound image 112.

In one embodiment, the ultrasound image 112 as displayed is considered a graphical user interface element, which may have a set of user interface/image processing functions pre-associated with the graphical user interface element, regardless of the content of the ultrasound image 112.

In one embodiment, the ultrasound image 112 as displayed is considered a graphical user interface element, which may have a set of user interface/image processing functions associated with the graphical user interface element based on the certain properties of the ultrasound image 112. The properties of the ultrasound image 112 may be based on a statistical analysis of the ultrasound image 112 (e.g., brightness, contrast) or based on a pattern recognition analysis of ultrasound image 112 (e.g., predefined tissue features captured in the ultrasound image 112). Different portions of the ultrasound image 112 that have different image characteristics and/or captured features or image patterns may be assigned dynamically with different graphical user interface functions.

In one embodiment, the properties of the ultrasound image 112 are determined in response to touch input and used to determine the graphical user interface functions to be invoked in response to the touch input. The properties are determined based on the entire ultrasound image 112 as displayed in one embodiment or alternatively, based on a portion of the ultrasound image 112 as identified via the touch gesture.

For example, in one embodiment, when a portion of the ultrasound image 112 as identified via the touch gesture has a contrast level below a threshold, the touch gesture is interpreted as a request to improve the contrast level, and when the contrast level is with a predetermined range, the touch gesture is interpreted as a request to perform edge enhancement on the ultrasound image 112, if there are detected edge in the area touched by the hand 110 of the user (or a stylus).

In one embodiment, the ultrasound image 112 is analyzed to generate a scale of operation; and the touch gesture is interpreted based on the scale of operation to generate parameters for an image processing operation that is performed as a response to the touch gesture.

When the touch input/gesture is interpreted based on the context provided by the image properties and/or features captured in the ultrasound image 112, the user interface can process the touch input more intelligently.

Figure 3:
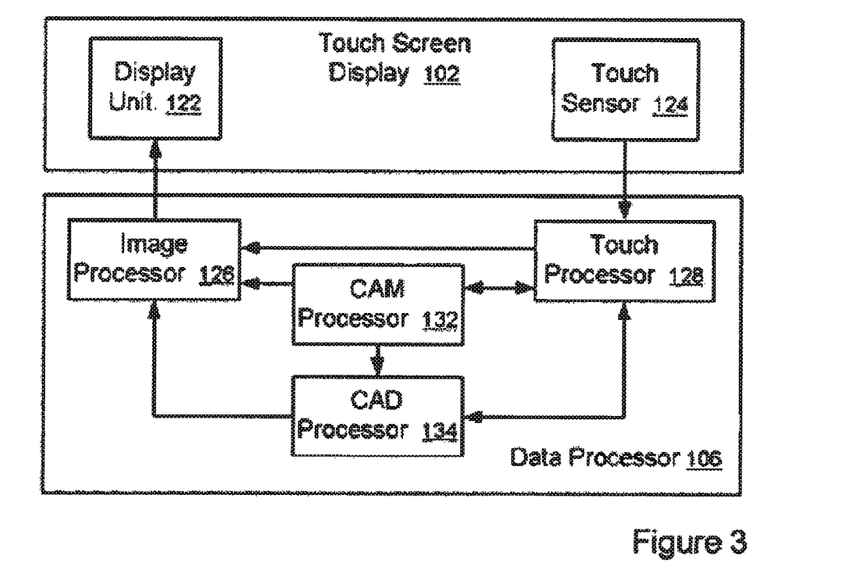
FIG. 3 shows a portion of an ultrasound imaging system configured to process touch input for computer aided measurement and/or computer aided diagnosis according to one embodiment.

FIG. 3 shows a portion of an ultrasound imaging system configured to process touch input for computer aided measurement and/or computer aided diagnosis according to one embodiment. In FIG. 3, the touch screen display 102 includes a display unit 122 configured to display images and a touch sensor 124 configured to detect touch input on the display unit 122.

In one embodiment, the touch sensor 124 is configured for the measurement of the locations over the display unit touched by one or more human fingers, or any pointing objects. In one embodiment, the touch sensor 124 is also configured for the measurement of the pressure of the touch. Various touch sensing technologies, currently known in the field and developed in the future, can be used in various embodiments of the touch sensor 124. The disclosure is not limited to a particular type of touch sensing technique.

In FIG. 3, the data processor 106 includes an image processor 126 configured to generate images for display on the display unit 122 (e.g., based on the signal input from the ultrasound transducer 104). The data processor 106 further includes a touch processor 128 configured to process the touch input generated by the touch sensor 124. The touch sensor 124 is configured to generate processing commands in response to the touch input received from the touch sensor 124.

In one embodiment, the touch processor 128 is configured to generate commands based on not only the touch input received from the touch sensor 124, but also the image information received from the image processor 126.

In one embodiment, the ultrasound image 112 displayed on the display unit 122 is analyzed to provide an image context; and the touch sensor 124 is configured to interpret the touch input based on the image context to identify, select, or generate a context sensitive processing command for the image processor.

In one embodiment, the image context is determined based on a portion of the touch input. For example, a touch input may specify one or more locations or a region; and the touch processor 128 is configured to request the image processor to obtain the image context based on the one or more locations or a region in the ultrasound image 112; and the image context is further used to interpret the remaining portion of the touch input to transform the ultrasound image 112.

Examples of the image context include the brightness level of the ultrasound image 112, the contrast level of the ultrasound image 112, a pattern recognized as being corresponding to a feature (e.g., a bone, an organ, and a tumor), the location and/or size of the recognized feature, etc.

For example, in one embodiment, a touch input at a location corresponding to a recognized feature may be interpreted as a request to adjust the zoom level and the center point to present the recognized feature using the available display area on the display unit 122, when the recognized feature is currently displayed in a small area of the display unit.

For example, in one embodiment, when a touch input is at an ultrasound image having a contrast level lower than a predetermine threshold but not at a location on a recognized feature, the touch input is interpreted as a request to adjust the contrast level of the ultrasound image 112.

Thus, in one embodiment, the touch processor 128 takes the user inputs originated from the touch sensor 124 of the touch screen display 102 and image information derived by the image processor from the ultrasound image 112 currently being displayed to on the display unit 122 of the touch screen display 102 to intelligently generate commands or instructions to operate the image processor 126 and/or the ultrasound imaging system 100.

In one embodiment, the user inputs originated from the touch sensor 124 and combined with the image information for the determination of the commands or instructions include the inputs from the area currently used to display the ultrasound image 112 and/or the inputs from the area configured to display graphical user interface elements, such as icon buttons, menu buttons, sliders, etc.

In one embodiment, in response to the user touch input, the data processor 126 is configured to generate one or more conventional graphical user interface elements, such as buttons, sliders, text input boxes, etc., which are temporarily displayed over the ultrasound image 112 to further collect user inputs. In one embodiment, the displayed conventional graphical user interface elements overlaid on the ultrasound image 112 is translucent, allowing the user to partially see ultrasound image 112 through the displayed conventional graphical user interface elements. The translucent graphical user interface elements provide hints to assist the user in providing input.

For example, when there are ambiguities regarding to the intent of the user, a plurality of choices can be presented to allow the user to select one from a plurality of possible processing options.

For example, when there are multiple processing options of similar priorities, the options can be displayed for an explicit selection by the user.

For example, the graphical user interface elements may be presented in one embodiment to receive user specified parameters for an operation selected based on the image context and the previous touch input.

Various types of image information can be derived from either a local region of the ultrasound image 112 touched by the user or the entire ultrasound image 112. The derived image information, which is typically different from the ultrasound image 112 itself, can be used by the touch processor 128 to deduce optimal commands for controlling the image processor 126 and/or the ultrasound imaging system 100. In one embodiment, the deduced commands may cause the image processor 126 to perform a local image processing operation within the local region identified via user touching or a global image processing operation for the entire ultrasound image 112.

Examples of the image processing operations include imaging parameter adjustment, zooming, translation, measurement, editing, deletion, copying, and combinations of such image processing operations. The imaging parameter adjustment can be applied to a local region touched by the user or the global ultrasound image 112. Examples of the imaging parameters that may be adjusted via such touch inputs include spatial resolution, temporal resolution, contrast, dynamic range, focal point, display depth, gain, time gain control (TGC), pulse repetition frequency (PRF), etc.

In one embodiment, the touch processor 128 is configured to determine the touch direction, speed, position, pressure, order of multiple touch operations, and combinations of multiple touch operations to determine an image processing operation intended by the user.

Examples of image information and properties that can be used as the image context for the determination of the image processing operation intended by the user include statistics data, such as mean brightness, noise level, different tissue texture, tissue motion, boundary, etc.

In one embodiment, the touch processor 128 is configured to detect one or more input signals from the touch sensor 124 of the touch screen display 102; and in response, the touch processor 128 analyzes the input signals to recognize one or more predefined touch gestures. The touch processor 128 optionally instructs the image processor 126 to process and analyze the currently displayed ultrasound image 112 to obtain image analysis results. Based on the image analysis results and the recognized touch gestures, the touch processor 128 is configured to generate one or more commands instructing the image processor 126 to transform the ultrasound image 112 or adjust the mode or parameters to generate the ultrasound image 112.

In one embodiment, the touch processor 128 provides the recognized touch gesture to the image processor 126; and the image processor 126 is configured to use the image analysis results and the recognized touch gesture to determine the one or more commands for transforming the ultrasound image 112, or adjusting the mode or parameters to generate the ultrasound image 112.

Examples of image analyses to obtain image context for the determination of the one or more commands include, but not limited to, filtering, statistical analyses, feature exaction, edge detection, and pattern recognition. For instance, local image mean brightness can be computed for image based dynamic gain control (DGC) adjustment.

Examples of the determined command include, but not limited to, image optimization, edge enhancement, restoration, segmentation, and imaging parameter adjustment.

In FIG. 3, the data processor 106 further includes a computer aided measurement (CAM) processor 132 and a computer aided diagnosis (CAD) processor 134, each coupled with the touch processor 128 to receive data and/or commands generated based on the touch input detected by the touch sensor 124.

Although FIG. 3 illustrates an embodiment that includes both the CAM processor 132 and the CAD processor 134, the data processor 106 of FIG. 1 in some embodiments has the CAM processor 132 but not the CAD processor 134; and in other embodiments, the data processor 106 of FIG. 1 in some embodiments has the CAD processor 134 but not the CAM processor 132.

In FIG. 3, the CAD processor 134 receives input from the CAM processor 132 for improved performance and user experience.

In one embodiment, the CAM processor 132 is implemented as specialized software and/or firmware running on one or more general purpose or special purpose microprocessors. The CAM processor 132 can also be implemented as a special purpose digital circuit without software and/or firmware instruction. The CAM processor 132 is configured to assist the user to perform various measurements based on the touch input result processed by the touch processor 128. The CAM processor 132 may provide feedback to the touch processor 128 to adjust the way the touch processor 128 processes the touch inputs.

For example, the touch processor 128 may interpret certain touch inputs as user identification of geometric input relative to the ultrasound image 112 presented on the touch screen. The geometric input may include one or more points, one or more line/curve segments, and one or more regions. The CAM processor 132 is configured to determine one or more measurement based on the geometric input, provided by the touch processor 128 according to the signals for the touch sensors.

In one embodiment, the CAM processor 132 is capable of measuring, based on the user touch input, parameters such as distance, perimeter, angle, ratio, area, volume, velocity, peak, heart rate, and auto trace, etc.

In one embodiment, the touch processor 128 is configured to interpret a predetermined touch gesture as a request to perform a measurement, and one or more subsequent touch inputs as geometric parameters for the measurement. The CAM processor 132 is configured to determine the measurement and instruct the image processor 126 to generate, on the display unit 122, a visual feedback of the geometric parameters used in the calculation. Based on the visual feedback, the user may determine whether the measurement as specified via the previous touch input is of sufficient accuracy. If the user determines that the visual feedback indicates inaccuracy in the geometric parameters specified via the previous touch input, the user may provide further touch input to adjust to geometric parameters. For example, in one embodiment, the visual feedback represents new user interface elements that can be selected to fine tune the parameters. The user interface dynamically adjusts the sensitivity and/or the scale for the fine tuning of the parameters. Thus, the user can easily provide accurate geometric parameters through a few iterations of touch inputs at different scale and sensitivity.

In one embodiment, the CAD processor 134 is implemented as specialized software and/or firmware running on one or more general purpose or special purpose microprocessors. The CAD processor 134 can also be implemented as a special purpose digital circuit without software and/or firmware instruction.

In one embodiment, the CAD processor 134 has two operating modes: interactive mode and automatic mode. In the interactive mode, the CAD processor 134 allows the user to influence the calculation performed by the CAD processor 134 using the touch screen inputs. In the automatic mode, the CAD processor 134 completes the diagnosis without considering any touch input received from the touch screen display 102.

In one embodiment, the CAD processor 134 performs a diagnosis through the operations of image preprocessing, image segmentation, image structure analysis, and structure classification.

Figure 4:
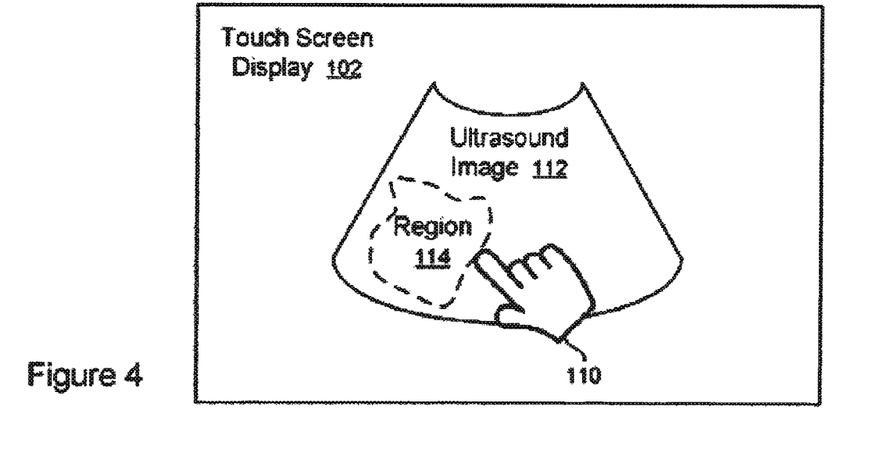
FIG. 4 illustrates an example of selecting a region for computer aided measurement and/or diagnosis according to one embodiment.

In one embodiment, the image analysis is performed for a local region within the ultrasound image 112 to obtain the image context for the determination of the one or more commands. For example, a user may draw an arbitrary shape via touching, using a hand 110 (or a stylus), to define a region of interest (ROI) 114 as illustrated in FIG. 4. After the region 114 is defined via touching, the user may further tap a point inside the region 114 to request the region 114 to be processed.

In one embodiment, the image processor 126 analyzes the region 114 of the ultrasound image 112 but not the region outside the region 114 to determine a local image context, based on which a processing command is determined for the tap at the point side the region 114.

In one embodiment, the image processor 126 analyzes the ultrasound image 114, including both the region 114 and the region outside the region 114, to determine a global image context, based on which a processing command is determined for the tap at the point side the region 114.

In one embodiment, the processing command, determined based on the local image content or the global image context, is applied to transform the region 114 within the ultrasound image 112, but not the region outside the region 114. Alternatively, the processing command can be applied globally to the entire ultrasound image 112.

In one embodiment, the region of interest (ROI) 114 has an arbitrary shape, determined according to the path of touch made via the hand 110 of the user. In one embodiment, the path of touch is converted into a regular shape, such as a box, an oval, a circle, etc., to simplify processing.

In one embodiment, the image analysis for the image context and/or the processing command to transform is applied to the live ultrasound images that are periodically updated according to the input from the ultrasound transducer 104. Alternatively, the image analysis and/or the processing command can be applied to a frozen image that is based on a particular set of input obtained from the ultrasound transducer 104 within a particular time period, where the input from the ultrasound transducer 104 is not updated with the passage of time.

In one embodiment, a dynamic ROI 114 is generated according to the location and motion of a user finger or a pointing device, such as a stylus. Image analysis performed within the ROI 114 to obtain the image context may be the operation of filtering, statistical analyses, feature exaction, edge detection, and pattern recognition, etc to obtain local image context. Such local image analysis can be applied to the live ultrasound image 112 or a frozen ultrasound image 112.

In one embodiment, after a dynamic ROI 114 is identified, an adaptive image optimization process is applied to the local image inside the ROI 114 as a response to a tap on a point inside the region 114. For instance, in response to the tap on the point inside the region 114, edge enhancement is applied if the ROI 114 contains boundaries; or a smoothing filter is applied if the ROI 114 has a speckle noise level above a threshold. Thus, the results of the boundary detection and speckle noise level evaluation performed on the ROI 114 provide the image context for the selection of the edge enhancement operation and/or the smoothing filter operation, as a response to the touch input on the ROI 114 from the user.

In one embodiment, after the touch sensor 124 detects one or more touch inputs, the touch processor 128 analyzes the touch inputs to identify one or more instructions represented by the touch input. The CAM processor 132 performs initial measurement based on the output of the touch processor 128 and then instructs the image processor 126 to display the measurement results and the geometric parameters used for the computation of the measurement results. If based on the visual feedback of the geometric parameters and the measurement results, the user determines that the measurement is acceptable, the user may provide a touch input to accept the measurement. In some embodiments, the measurement is accepted if the user does not provide a touch input to reject the measurement. If the user observes inaccuracy in the visual feedback, the user may refine the measurement process with additional touch screen based instructions. The refinement can be local or global. For example, if the user wants to modify one corner of a border, the user interface allows the user to readjust the border line with a touch of the touch screen display 102 with one finger or any stylus type tool. For example, the user interface allows the user to use two fingers to touch the touch screen display 102 and reduce or increase the distance between the touch points of the two fingers to reduce or increase the size of a closed border. For example, the user interface allows the user to touch a border representation displayed on the touch screen display 102 and move the touch point to adjust the border of a fetal head.

In one embodiment, after the touch sensor 124 generates touch signals in response to user touch on the touch screen display 102, the touch processor 128 analyzes the touch signals to identify one or more input instructions corresponding to the touch signals. The CAM processor 132 performs an automatic measurement based on the one or more input instructions and then instructs the image processor 126 to display the result of the automatic measurement. For example, if it is detected that the user touches a place inside an object shown in the ultrasound area 112 of the touch screen display, the CAM processor 132 analyzes the ultrasound image 112 to automatically detect the border of the object as shown in the ultrasound image 112 and measures the diameter, perimeter, and/or area of the object defined by the border. The object can be a heart chamber, a fetal head, bladder, gall bladder, or other organs and lesions. The detected border is drawn on over the ultrasound image 112 to provide a visual feedback of the detected border that is used as a geometric parameter for the computation of the measurements. Based on the visual inspection of the alignment between the visual feedback of the border used in the calculation and the underline object as in the ultrasound image, the user may decide to accept the measurement or reject the measurement. The user may indicate the decision to accept or reject the measurement result using a touch gesture performed on the touch screen. The user interface may allow the user to touch the visual feedback of the border and move the touch point to adjust the border. The user interface may allow the user to draw a region of interest (ROI) 114 to limit the border detection operation with the region of interest 114, or suggest an initial estimate of the border; and the CAM processor 132 performs the measurement of the desired parameters based on the region of interest 114 drawn by the user via the touch of the touch screen display 102. For instance, intima-media thickness (IMT) measurement can be done in such a way.

In one embodiment, after the touch sensor 124 generates touch signals in response to user touch on the touch screen display 102, the touch processor 128 analyzes the touch signals to identify one or more input instructions corresponding to the touch signals. In response to the one or more input instructions, the CAD processor 134 performs an automatic diagnosis and then displays the results. For example, the CAD processor 134 detects a lesion in an organ and displays diagnostic information about the lesion based on the properties of the lesion and the disease knowledge database on the system. The properties may include size, shape, orientation, border smoothness, contrast ratio, and acoustic shadow. The diagnostic information may display that the detected lesion is a tumor with a specific level of confidence. The CAD processor 134 may instruct the image processor 126 to draw geometric elements illustrating the properties, such as size, shape, orientation, etc., that are used in the diagnosis for visual confirmation by the user.

In one embodiment, after the touch sensor 124 generates touch signals in response to user touch on the touch screen display 102, the touch processor 128 analyzes the touch signals to identify one or more input instructions corresponding to the touch signals. In response to the one or more input instructions, the CAD processor 134 performs diagnoses with input from the user in an interactive way. For instance, the CAD processor 134 may show a segmented lesion and display some diagnostic data and information on the screen for the user to determine whether the results are satisfactory. If not, the user can adjust the CAD algorithm, input new instructions using the touch screen, and then rerun the diagnosis. For example, the visual feedback of the geometric parameters used in the diagnosis can be overlaid on the ultrasound image 112; and the user may determine whether the diagnosis identified by the CAD processor 134 is acceptable based on the alignment in position, shape, orientation, size, etc, between the visual feedback of the geometric parameters used in the diagnosis and the underline ultrasound image 112 displayed on the touch screen display 102. If misalignment is visually detected by the user, the user interface allows the user to provide touch input to adjust the geometric parameters to assist the CAD processor 134 to make an improved diagnosis.

In one embodiment, after the touch sensor 124 generates touch signals in response to user touch on the touch screen display 102, the touch processor 128 analyzes the touch signals to identify one or more input instructions corresponding to the touch signals. In response to the one or more input instructions, the CAM processor 132 performs an initial measurement and instructs the image processor 126 to display the measurement results, together with visual feedback of the geometric parameters used in the measuring operation. The visual feedback is overlaid on the ultrasound image to allow the user to inspect the quality of the geometric parameters used in the measuring operation. If the user decides not to accept the measurement result, the user may refine the measurement process by providing touch inputs to adjust the geometric parameters, and if the user decides to accept the measurement result, as indicated via a touch input on the touch screen display 102, the CAD processor 134 proceeds to make a diagnosis. Based on the touch input made to accept the measurement generated by the CAM processor 132, the CAD processor 134 may operate in an automated way, or in an interactive way. When running in an interactive mode, the CAD processor 134 makes diagnoses using the measurement results from the CAM processor 132 and the touch input provided by the user using the touch screen display 102.

Through at least some of the arrangements discussed above, the measurement can be performed on the ultrasound imaging system 100 more intuitively, due to the combination of touch screen user interface and CAM processor. Further, the use of a CAD processor in an interactive mode overcomes the limitation of both pure CAD and manual diagnostic processes. The combination of the CAD processor and the CAM processor improves the accuracy of diagnosis and provides an intuitive user experience.

Figure 5:
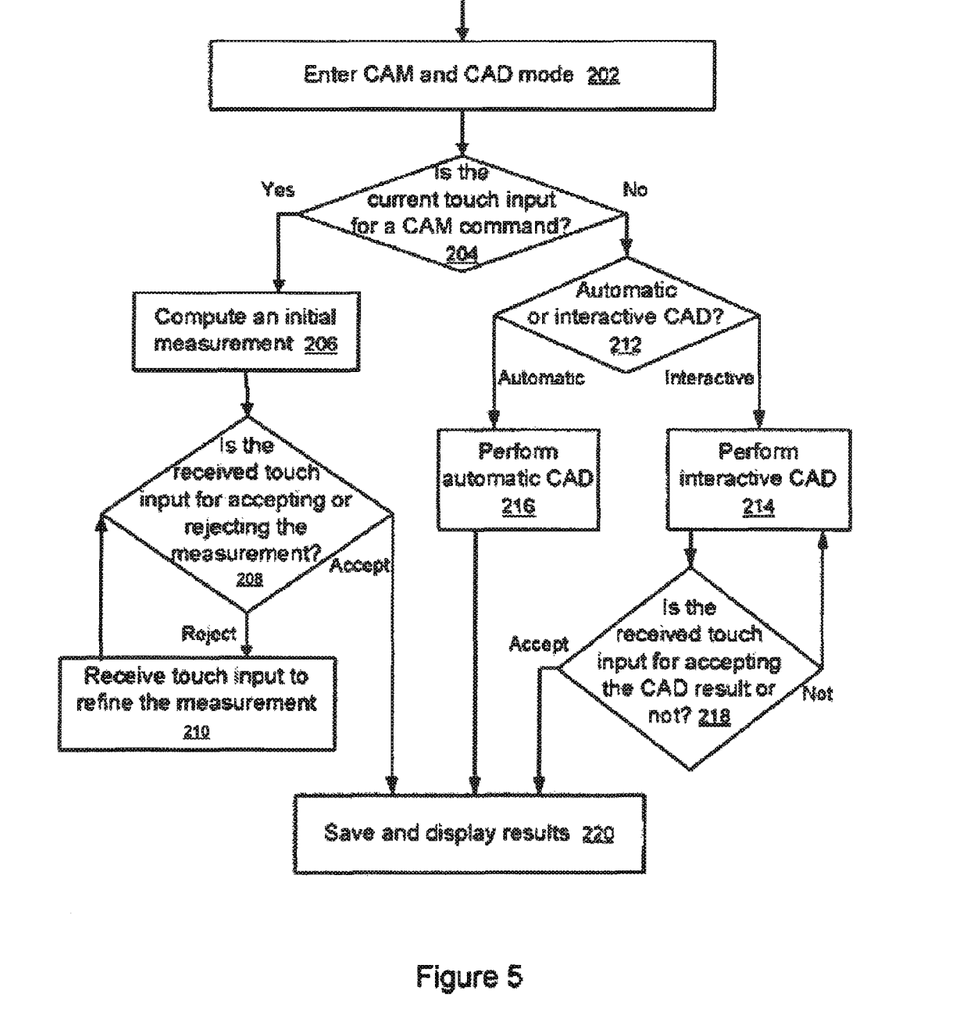
FIG. 5 shows a method to perform computer aided measurement or diagnosis according to one embodiment.

FIG. 5 shows a method to perform computer aided measurement or diagnosis according to one embodiment. In FIG. 5, after the ultrasound imaging system 100 enters the CAM and CAD mode (e.g., via the selection of a menu option, or via a touch gesture performed over the ultrasound image 112 on the touch screen display 102), the touch processor 128 determines 204 whether the current touch input is for a CAM command.

If it is determined 204 that the current touch input is for a CAM command, the CAM processor 132 computes 206 an initial measurement. The result of the initial measurement and the geometric parameters, such as points, lines, curves, areas, etc., that are used in the computation of the initial measurements are displayed over the ultrasound image 112 by the image processor 126.

If it is determined that the user rejects, or does not accept, the measurement results (208), the touch processor 128 is configured to receive and process touch inputs to refine the measurement (210); otherwise, the ultrasound imaging system 100 saves (220) and displays the measurement results accepted by the user.

If it is determined 204 that the current touch input is for a CAD command, the touch processor 128 further determines 212 whether the CAD processor 134 is instructed to run in an automatic mode, or in an interactive mode.

If it is determined 212 that the CAD processor 134 is instructed by the user to run in an automatic mode, the CAD processor 134 performs automatic computed aided diagnosis and instruct the image processor 126 to display 220 the results, without considering touch input between the starting point of the automatic computed aided diagnosis and the display of the diagnosis result.

If it is determined 212 that the CAD processor 134 is instructed by the user to run in an interactive mode, the CAD processor 134 performs interactive computer aided diagnosis, in which the CAD processor 134 is to receive at least one input from the touch processor 128, responsive to at least one user touch, between the starting point of the automatic computer aided diagnosis and the display of the diagnosis result. The result of the initial diagnosis and the geometric parameters, such as points, lines, curves, areas, etc., that are used in the computation of the initial diagnosis are displayed over the ultrasound image 112 by the image processor 126. The touch processor 134 is configured to determine whether the received touch input is for accepting the CAD result. If it is determined 218 that the received touch input is not for accepting the CAD result, the touch processor 128 processes further touch inputs to adjust parameters for the CAD processor 134 to refine diagnosis result.

If it is determined 218 that the received touch input is for accepting the CAD result, the diagnosis result is saved 220.

Figure 6:
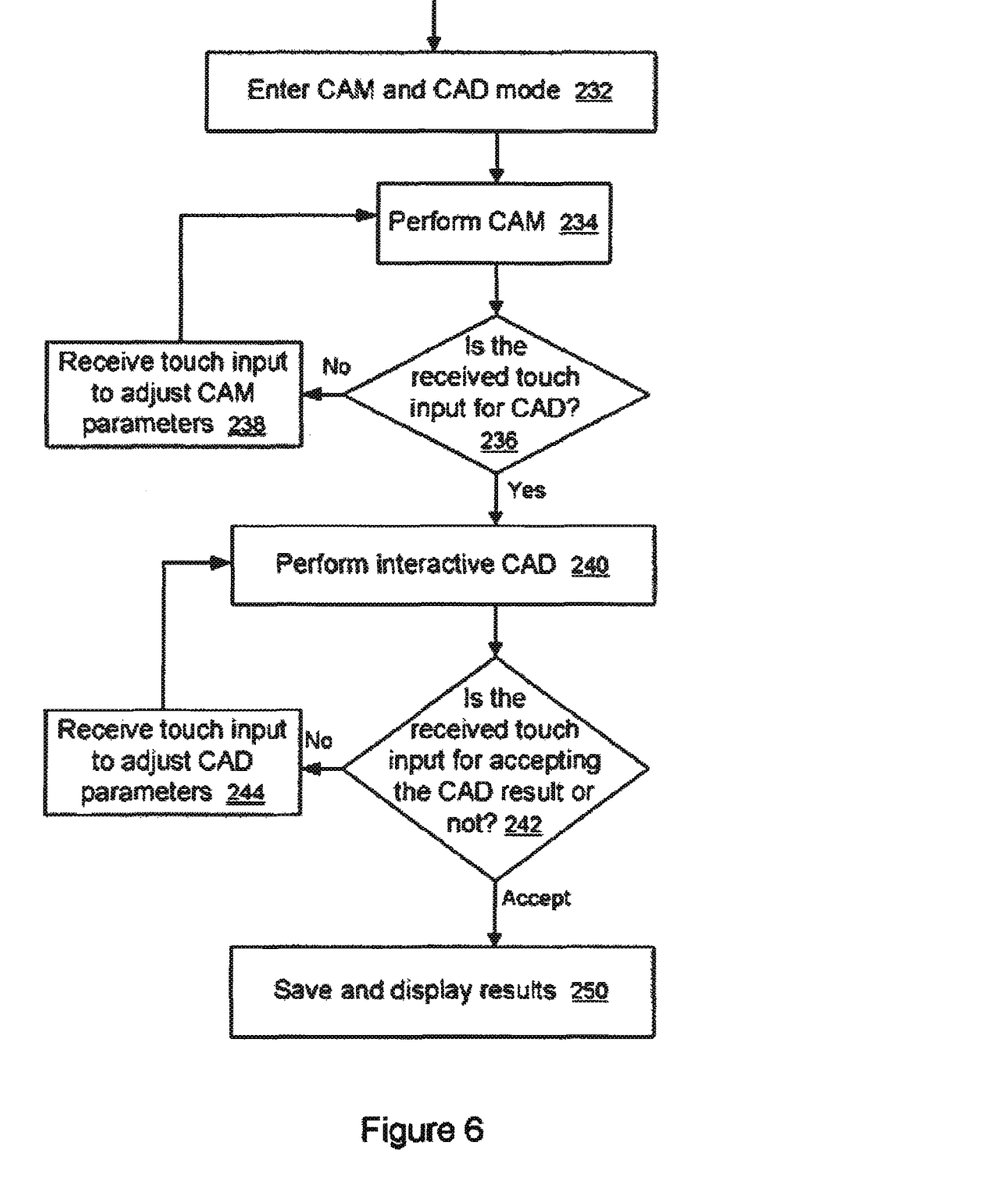
FIG. 6 shows a method to perform computer aided measurement and diagnosis according to one embodiment.

FIG. 6 shows a method to perform computer aided measurement and diagnosis according to one embodiment. In FIG. 6, after the ultrasound imaging system 100 enters the CAM and CAD mode (e.g., via the selection of a menu option, or via a touch gesture performed over the ultrasound image 112 on the touch screen display 102), the touch processor 128 instructs the CAM processor 132 to perform one or more measurement 234. The touch processor 128 then determines whether the currently received touch input is for CAD; and if not, the touch processor 128 is configured to receive 238 and process touch input to adjust CAM parameters for the CAM processor 132 to perform one or more measurement 234.

If it is determined 236 that the currently received touch input is for CAD, the CAD processor 134 is instructed to perform interactive CAD 240. After a diagnosis is reached using a set of geometric parameters, the touch processor 128 determines 242 whether the currently received touch input for accepting the CAD result or not; and if not, the touch processor 128 is configured to receive 244 and process touch input to adjust CAD parameters for the CAD processor 134 to perform 240 interactive CAD.

In one embodiment, one or more other input devices, such as a mouse, a keyboard, a switch, a voice recognition system, etc., can be used in combination with the touch screen display 102 to receive input signals corresponding to at least some of the input parameters discussed in the present disclosure. For example, the determination of whether 204 the measurement is to be accepted or rejected can be based on a touch input, an input signal from a switch, keyboard, mouse, or a voice recognition system. For example, the determination of whether 218 to accept the CAD result can be based on a touch input, an input signal from a switch, keyboard, mouse, or a voice recognition system. For example, the determination of whether 204 the current command is for a CAM command can be based on a touch input, an input signal from a switch, keyboard, mouse, and/or a voice recognition system. For example, the determination of whether 212 the current command is for an automatic or interactive CAD command can be based on a touch input, an input signal from a switch, keyboard, mouse, and/or a voice recognition system. For example, the determination of whether 236 the current input is for CAD can be based on a touch input, an input signal from a switch, keyboard, mouse, and/or a voice recognition system. For example, the determination of whether 242 the received input is for accepting the CAD result or not can be based on a touch input, an input signal from a switch, keyboard, mouse, and/or a voice recognition system. In one embodiment, a combination of the input from two or more input devices is used to indicate a signal to invoke a command or represent an input parameter. Some of the input commands or parameters discussed in the present disclosure can be detected or determined based on a predetermined pattern of input signals from one or more input devices, which may include some of the devices, such as the touch screen display 102, a mouse, a keyboard, a switch, a voice recognition system, a trackball, a touch pad, a joystick, etc. In one embodiment, at least some of the touch inputs discussed above is in connection with input signals from one or more other devices. In one embodiment, at least some of the touch inputs discussed above can be replaced with inputs from input devices other than the touch screen display 102. In one embodiment, the ultrasound imaging system 100 includes one or more such input devices, but not others. Some of the commands and/or input parameters can be based on one or input devices without using the touch screen display 102. Thus, the disclosure is not limited to receiving input solely from the touch screen display 102.

In one embodiment, at least a portion of the touch input discussed above in connection with the operation of the CAM processor 132 and the CAD processor 134 is received from an area of the display unit 122 of the touch screen display 102, on which area the ultrasound image 112 is displayed.

In one embodiment, at least a portion of the touch input is received from an area that is outside the ultrasound image 112 and that displays graphical representation of user interface elements that are separate from the ultrasound image 112.

In one embodiment, at least a portion of the touch input is received from a graphical representation of one or more user interface elements overlaid in a partially transparent manner over the ultrasound image 112.

In one embodiment, at least a portion of the touch input identifies a region 114 of interest within the ultrasound image 112.

In one embodiment, the image processor 126, the touch processor 128, and the CAD processor 134 are implemented using separate hardware. For example, the image processor 126, the touch processor 128, the CAM processor 132, and/or the CAD processor 134 can be implemented using application-specific integrated circuit (ASIC) or field-programmable gate array (FPGA). Alternatively, the image processor 126, the touch processor 128, the CAM processor 132, and/or the CAD processor 134 can be implemented using general purpose microprocessor controlled by firmware and/or software. In one embodiment, the image processor 126, the touch processor 128, the CAM processor 132, and the CAD processor 134 are configured to share one or more microprocessors.

Thus, at least one embodiment of the disclosure provides an ultrasound imaging system configured with a touch screen based user interface, which addresses at least one of the limitations and/or problems in the conventional medical ultrasound imaging system equipped with touch screens.

An ultrasound imaging system according to one embodiment of the disclosure includes an ultrasound transducer 104, a touch screen display 102, a beamformer 108, a data processing unit (e.g., data processor 106) and an electronic circuit interconnecting the components.

In one embodiment, the data processing unit is configured to perform signal processing, image processing, and input/output handling.

In one embodiment, the input/output handling includes receiving touch input from the image area displayed on the touch screen display and using image information derived from the ultrasound image 112 currently being displayed on the touch screen display 102 to generate intelligently proper commands or instructions corresponding to the touch input.

In one embodiment, in response to the touch input received from the image area, the touch input is processed and analyzed to determine the intended instructions by the user. According to the determined instructions by the user, an image analysis is performed to derive image information from either a local region of the image presented on the image area of the touch screen display 102, or the entire ultrasound image 112. Based on the derived image information, one or more commands are then generated to perform imaging tasks for the processing the live or frozen ultrasound image 112.

In one embodiment, the commands determined in accordance with the touch input and the derived image information are executed for local image processing within a location region 114 identified by the user touch input. Alternatively or in combination, the commands may be executed for global image processing of the entire ultrasound image 112.

In one embodiment, a local region is predefined or preselected. In one embodiment, a local region 114 is defined or selected by the user via touch input. In one embodiment, the local region is where the user is touching (e.g., via simultaneously touching multiple points using multiple fingers, via sequentially touching a set of discrete points using one finger, or via sliding one or more fingers on the touch screen); and the image in the local region is a portion of the ultrasound image 112 displayed on the touch screen display 102.

Limiting the processing of the image to a local region reduces the processing load on the data processing unit and can improve the response time. Thus, the result of the image processing can be provided in real time as the user providing input via touch input. For example, when the global image has 500×600 pixels and the local image has 20×30 pixels, the time used for the processing of the local image can be much shorter than that for the global image.

In one embodiment, the image processing operations associated with the determined instructions include imaging parameter adjustment, zooming, translation, measurement, editing, deletion, and copying. The imaging parameter adjustment can be either local or global.

In one embodiment, a local image processing operation is applied to the portion of image that is displayed within a predefined region (e.g., the image area of the touch screen, or a portion of the image area of the touch screen); and a global image processing operation is applied to the entire ultrasound image which may have a portion that is outside the predefined region.

In one embodiment, the imaging parameters that can be adjusted via the determined instructions include spatial resolution, temporal resolution, contrast, dynamic range, focal point, display depth, gain, time gain control (TGC), pulse repetition frequency (PRF), etc.

In one embodiment, the data processing unit is configured to detect direction, speed, position, pressure, and order of user operations, and combinations of multiple user touch inputs. The detected direction, speed, position, pressure, and order of user operations, and combinations of multiple user touch inputs are used to determine the intended instructions of the user.

In one embodiment, the image information and properties that can be displayed in accordance with the intended instructions of the user include statistics such as mean brightness, noise level, different tissue texture, tissue motion, boundary, etc.

In one embodiment, the data processing unit is configured to detect input signal from the touch screen, analyze the input signal to determine the intended instruction of the user, process and analyze the displayed ultrasound image in accordance with the determined instruction of the user, and provide an output on the touch screen display based on the input instruction and the result of the image analysis.

In one embodiment, the touch input of the user can be generated not only from the control area of the touch screen, but also the image area of the touch screen.

In one embodiment, the properties of ultrasound image are processed and analyzed, and then combined with the user input instructions from the touch screen to generate proper commands, such as an optimal command that will be carried out to perform certain tasks, such as image enhancement. For example, the local image brightness is determined and used in one embodiment to generate gain adjustment commands for processing a local region of the ultrasound image in accordance with a touch input received in the image region of the touch screen display.

In one embodiment, local image processing and optimization are performed in response to the determined user instruction and based on local image properties.

In one embodiment, the touch screen operations are reconfigurable. The user can change or redefine some or all of predefined touch screen operations. For instance, a left-to-right move can be redefined as brightness increase instead of the default meaning: forward replay.

In one embodiment, after a touch input requesting reconfiguration is received from the touch screen display 102, the touch processor 128 analyzes and recognizes touch inputs that are provided by the user as the training inputs. The training inputs are used to determine parameters for recognizing subsequent touch inputs that are intended to signal the user request corresponding to the instruction or command that is being reconfigured. Thus, the touch recognition for the instruction or command, corresponding to a touch gesture is reconfigured based on the training results.

In one embodiment, for instance, in the default setting, pressing a point on an image with a finger tip for a certain amount of time like 2 seconds brings transmitting focus to the nearest location of the finger tip; the same operation can be reconfigured to perform a different task like drawing a box of a predetermined size corresponding to a region 114 of interest.

In the above discussion, examples of touch screen input processing are presented in connection with ultrasound imaging systems. However, the touch screen image processing techniques can also be applied to other types of imaging systems and systems configured for displaying images, such as computed axial tomography (CAT or CT) systems, magnetic resonance imaging (MRI) systems, photoacoustic imaging systems, etc.

In the foregoing specification, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

What is claimed is:

1. An ultrasound imaging apparatus, comprising:
   a touch screen display to display an ultrasound image;
   a touch processor coupled with the touch screen display to receive from a user a touch input from a portion of the ultrasound image currently being displayed;
   a computer aided measurement (CAM) processor coupled with the touch processor to measure the ultrasound image; and
   a computer aided diagnosis (CAD) processor coupled with the touch processor to diagnose the ultrasound image;
   wherein:
      the ultrasound imaging apparatus enters a CAD and CAM mode;
      the touch processor determines whether the touch input instructs running a CAM command or a CAD command;
      upon receiving the determination that the touch input instructs running a CAM command, the CAM processor performs an initial measurement on the ultrasound image, provides a first measurement result to the touch screen display for the user to review, and performs a refined measurement on the ultrasound image and provides a second measurement result based on ascertaining that the user rejects the first measurement result; and
      upon receiving the determination that the touch input instructs running a CAD command, the CAD processor ascertains whether the touch input instructs running an automatic CAD mode or an interactive CAD mode, and upon ascertaining that the touch input instructs running an interactive CAD mode, performs an interactive diagnosis on the ultrasound image based on receiving at least one touch input from the user indicating the user's acceptance or rejection of a result of the interactive diagnosis and based on the first measurement result or the second measurement result provided by the CAM processor.

2. The ultrasound imaging apparatus of claim 1, wherein upon ascertaining that the touch input instructs running an automatic CAD mode, the CAD processor performs an automatic diagnosis on the ultrasound image and displays on the touch screen display a result of the automatic diagnosis.

3. The ultrasound imaging apparatus of claim 1, wherein the CAM processor performs the refined measurement on the entire ultrasound image or a local region of the ultrasound image touched by the user.

4. The ultrasound imaging apparatus of claim 1, wherein upon determining that a current touch input received on the touch screen display is for accepting a measurement result provided by the CAM processor, the touch processor instructs the CAD processor to perform the interactive diagnosis on the ultrasound image.

5. The ultrasound imaging apparatus of claim 1, wherein when running the interactive CAD mode, the CAD processor receives the at least one touch input from the user via the touch processor between starting of the interactive diagnosis and presentation of a user accepted result for the interactive diagnosis.

6. The ultrasound imaging apparatus of claim 1, wherein the CAM processor is coupled with the image processor to present on the touch screen display one or more parameters used for producing a measurement result.

7. The ultrasound imaging apparatus of claim 6, wherein the one or more parameters are overlaid on the ultrasound image.

8. The ultrasound imaging apparatus of claim 7, wherein the touch processor determines whether a currently received touch input is for adjusting the one or more parameters, or for accepting the measurement result.

9. The ultrasound imaging apparatus of claim 1, wherein the CAD processor is coupled with the image processor to present on the touch screen display one or more parameters used for producing a diagnosis result.

10. The ultrasound imaging apparatus of claim 9, wherein the one or more parameters are overlaid on the ultrasound image.

11. The ultrasound imaging apparatus of claim 10, wherein the touch processor determines whether a currently received touch input is for adjusting the one or more parameters, or for accepting the diagnosis result.

12. A computer-implemented method for computer aided measurement and diagnosis on an ultrasound image generated by an ultrasound imaging apparatus, comprising:
   entering a CAD and CAM mode;
   displaying, on a touch screen display of the ultrasound imaging apparatus, the ultrasound image;
   receiving from a user a touch input from a portion of the ultrasound image currently being displayed;
   determining whether the touch input instructs running a computer aided measurement (CAM) command or a computer aided diagnosis (CAD) command;
   upon determining that the touch input instructs running a CAM command:
      performing an initial measurement on the ultrasound image,
      providing a first measurement result to the touch screen display for the user to review, and
      performing a refined measurement on the ultrasound image and providing a second measurement result based on ascertaining that the user rejects the first measurement result; and
   upon determining that the touch input instructs running a CAD command:
      ascertaining whether the touch input instructs running an automatic CAD mode or an interactive CAD mode, and
      upon ascertaining that the touch input instructs running an interactive CAD mode, performing an interactive diagnosis on the ultrasound image based on receiving at least one touch input from the user indicating the user's acceptance or rejection of a result of the interactive diagnosis and based on the first measurement result or the second measurement result.

13. The computer-implemented method of claim 12, further comprising:

determining at least one of: a distance, a perimeter, an angle, a ratio, an area, a volume, a velocity, a peak, or a heart rate.

14. The computer-implemented method of claim 13, wherein performing the refined measurement on the ultrasound image comprises:
   performing the refined measurement on the entire ultrasound image.

15. The computer-implemented method of claim 12, wherein performing the refined measurement on the ultrasound image comprises:
   performing the refined measurement on a local region of the ultrasound image touched by the user.

16. The computer-implemented method of claim 12, further comprising:
   allowing the user to interactively adjust one or more geometric parameters via touching the touch screen display.

17. The computer-implemented method of claim 16, further comprising:
   dynamically adjusting sensitivity and scale of the adjustment of the one or more geometric parameters.

18. The computer-implemented method of claim 12, further comprising:
   determining one or more geometric parameters based on an initial touch input identifying a location or an area and based on an analysis of the ultrasound image.

19. A non-transitory computer readable medium storing instructions, when executed, cause an ultrasound imaging apparatus having a touch screen display to perform computer aided measurement and diagnosis on an ultrasound image generated by the ultrasound imaging apparatus:
   entering a CAD and CAM mode;
   displaying the ultrasound image on the touch screen display;
   receiving from a user a touch input from a portion of the ultrasound image currently being displayed;
   determining whether the touch input instructs running a computer aided measurement (CAM) command or a computer aided diagnosis (CAD) command;
   upon determining that the touch input instructs running a CAM command:
      performing an initial measurement on the ultrasound image,
      providing a first measurement result to the touch screen display for the user to review, and
      performing a refined measurement on the ultrasound image and providing a second measurement result based on ascertaining that the user rejects the first measurement result; and
   upon determining that the touch input instructs running a CAD command:
      ascertaining whether the touch input instructs running an automatic CAD mode or an interactive CAD mode, and
      upon ascertaining that the touch input instructs running an interactive CAD mode, performing an interactive diagnosis on the ultrasound image based on receiving at least one touch input from the user indicating the user's acceptance or rejection of a result of the interactive diagnosis and based on the first measurement result or the second measurement result.

* * * * *